United States Patent
Fukuma

(10) Patent No.: US 8,969,806 B2
(45) Date of Patent: Mar. 3, 2015

(54) DRUG INSPECTION DEVICE AND DRUG INSPECTION METHOD

(75) Inventor: Tomohiro Fukuma, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/129,798

(22) PCT Filed: Jun. 27, 2012

(86) PCT No.: PCT/JP2012/066446
§ 371 (c)(1),
(2), (4) Date: Dec. 27, 2013

(87) PCT Pub. No.: WO2013/002291
PCT Pub. Date: Jan. 3, 2013

(65) Prior Publication Data
US 2014/0145082 A1      May 29, 2014

(30) Foreign Application Priority Data
Jun. 28, 2011    (JP) .................................. 2011-143270

(51) Int. Cl.
*G01N 21/95*    (2006.01)
*G01J 3/06*    (2006.01)
(Continued)

(52) U.S. Cl.
CPC ............... *G01N 21/9508* (2013.01); *G01J 3/06* (2013.01); *G01N 21/359* (2013.01); *G01N 21/3563* (2013.01); *G01J 3/42* (2013.01); *G01N 21/85* (2013.01)
USPC .................................................. 250/339.07

(58) Field of Classification Search
CPC ................................................ G01N 21/9508
USPC ........................................ 250/339.07, 339.06
See application file for complete search history.

(56) References Cited

U.S. PATENT DOCUMENTS

| | | | | |
|---|---|---|---|---|
| 7,294,837 | B2 * | 11/2007 | Mertens et al. | 250/339.07 |
| 2006/0235621 | A1 * | 10/2006 | Cole et al. | 702/19 |
| 2009/0026373 | A1 | 1/2009 | Mertens et al. | |

FOREIGN PATENT DOCUMENTS

| | | |
|---|---|---|
| EP | 1 674 859 A1 | 6/2006 |
| JP | 2006-516722 A | 7/2006 |

(Continued)

OTHER PUBLICATIONS

International Search Report for PCT/JP2012/066446, dated Aug. 7, 2012.

(Continued)

*Primary Examiner* — David Porta
*Assistant Examiner* — Faye Boosalis
(74) *Attorney, Agent, or Firm* — Sughrue Mion, PLLC

(57) ABSTRACT

A drug inspection device and method for distinguishing tablets that have different amounts of active pharmaceutical ingredients and are indistinguishable in appearance. The device focuses on a tablet packaging process for tablets containing different amounts of active pharmaceutical ingredients, every row or every pocket, having housed therein a plurality of tablets, is used for conveyance. A beam having near-infrared light irradiates the tablets, a spectroscope receives reflected light, a near-infrared imaging unit captures a spectrum obtained through dispersion of the reflected light by the spectroscope and generates image data, and a control unit processes the image data and performs an operation for distinguishing the types of tablets. The control unit controls the near-infrared imaging unit to perform image capture at least once on the tablets included in the one row, to compute average spectrum data per tablet, and to distinguish the type of tablet based on the average spectrum data.

7 Claims, 6 Drawing Sheets

(51) Int. Cl.
*G01N 21/3563* (2014.01)
*G01J 3/42* (2006.01)
*G01N 21/359* (2014.01)
*G01N 21/85* (2006.01)

(56) References Cited

FOREIGN PATENT DOCUMENTS

| | | |
|---|---|---|
| JP | 2009-047687 A | 3/2009 |
| JP | 2009-244112 A | 10/2009 |
| JP | 2010-112887 A | 5/2010 |
| JP | 2010-175528 A | 8/2010 |
| JP | 2010-216890 A | 9/2010 |

OTHER PUBLICATIONS

Communication issued in EP Patent Application No. 12804932.7 dated Nov. 17, 2014.

* cited by examiner

DRUG INSPECTION DEVICE AND DRUG INSPECTION METHOD

CROSS REFERENCE TO RELATED APPLICATIONS

This application is a National Stage of International Application No. PCT/JP2012/066446, filed Jun. 27, 2012, claiming priority from Japanese Patent Application No. 2011-143270, filed Jun. 28, 2011, the contents of all of which are incorporated herein by reference in their entirety.

TECHNICAL FIELD

The present invention relates to a drug inspection device and a drug inspection method for distinguishing types of tablets in a tablet packaging process for tablets containing different amounts of active pharmaceutical ingredients, every row or every pocket, in which a plurality of rows each having aligned therein a plurality of tablets housed in respective pockets are conveyed.

BACKGROUND ART

Various methods have been considered in order to prevent tablets of different varieties from becoming mixed up in a tablet packaging process. For example, Patent Literature 1 proposes a method of analyzing whether tablets of different varieties have become mixed up by irradiating one row of tablets that passes through the packaging line with near-infrared light and analyzing the spectrum of reflected light using principal component analysis.

CITATION LIST

Patent Literature

[PTL 1] JP 2010-112887A

SUMMARY OF INVENTION

In the pharmaceutical industry, ethical drugs for hospitals and dispensing pharmacies and investigational drugs that are used in clinical testing and the like are manufactured, apart from OTC drugs that are commercially available. As for an investigational drug, normally a plurality of drugs in which the amounts of active pharmaceutical ingredients have been altered are prepared in order to verify the effects of the drug. For example, in the case of such a drug in tablet form, only the amounts of active pharmaceutical ingredients are different, and the tablets are manufactured so as to be indistinguishable in appearance. Then, after having been packaged in PTP sheets, tablets are removed and subject to destructive testing in order to check whether the correct tablets are housed in the correct positions. Specifically, some of the packaged PTP sheets are picked out, and some of the tablets are removed and subject to destructive testing to determine that tablets having different amounts of active pharmaceutical ingredients are housed every row or pocket. Destructive testing is generally performed using ultraviolet (UV) absorption spectrophotometry or high performance liquid chromagraphy (HPLC). Currently, this system in combination with testing has lead to the building of a quality assurance system, although it is desired to collect data that can complement the quality of investigational drugs in order to further strengthen this quality assurance system.

The present invention was made in order to resolve the above problems, and an object of invention is to provide a drug inspection device and a drug inspection method that are capable of distinguishing types of tablets that have different amounts of active pharmaceutical ingredients and are indistinguishable in appearance, such as tablets manufactured for clinical trials.

Technical Problem

A drug inspection device according to the present invention is for distinguishing types of tablets in a tablet packaging process for packaging tablets containing different amounts of active pharmaceutical ingredients, every row or every pocket, in which a plurality of rows each having aligned therein a plurality of tablets housed in respective pockets are conveyed, and includes an irradiation unit configured to irradiate the tablets with a light beam that includes near-infrared light, a spectroscope on which reflected light from the tablets is incident, a near-infrared imaging unit configured to capture a spectrum obtained through dispersion of the reflected light by the spectroscope and to generate image data, and a control unit configured to process the image data and to perform an operation for distinguishing the types of tablets. The near-infrared imaging unit is configured to capture, with one image capture, the spectrums of a predetermined number of pixels allocated to a predetermined length in a direction in which the tablets are aligned in the row, and the control unit is configured to perform control such that the near-infrared imaging unit performs image capture at least once on the tablets included in the one row, to compute average spectrum data per tablet by averaging the spectrums of the pixels on a tablet surface every pocket, and to distinguish the type of tablet based on the average spectrum data.

Investigational drugs in tablet form include those where a plurality of rows each including a plurality of tablets are provided, and tablets containing different amounts of active pharmaceutical ingredients are packaged every row or every pocket. In view of this, in the present invention, the near-infrared imaging unit is configured to capture, with one image capture, the spectrums of a predetermined number of pixels allocated to a predetermined length in the direction in which the tablets are aligned in the row, and is controlled so as to perform image capture on the tablets included in one row at least once. Average spectrum data that is obtained based on reflected light per tablet is computed, and the type of tablet is distinguished based on this data. Therefore, even tablets that have different amounts of active pharmaceutical ingredients and are indistinguishable in appearance can be distinguished by type. As a result, the quality of investigational drugs to be taken in tablet form by a subject can be fully guaranteed.

In the above processing, average spectrum data obtained by averaging the spectrums of the pixels is used, enabling the volume of data to be reduced and the type of tablet to be distinguished quickly. Also, the device is suited to data transmission by wireless or the like, enabling device versatility to also be improved. Furthermore, reducing the volume of data enables power savings to be realized, even with regard to the load on the computer that saves the series of measurement results.

With the above device, spectrums based on one or more pixels allocated on each tablet can be specified by various methods. For example, the control unit is able to specify in advance one or more pixels allocated on each tablet, and to distinguish the type of tablet based on the spectrums of the specified pixels. That is, the device specifies in advance which pixels are allocated on the tablet, from among the plurality of allocated pixels. For example, the device is able to specify such pixels in advance, based on the conveyance speed of the tablets, the interval between pockets, the allocation interval of pixels, and the like.

Alternatively, the control unit is also able to specify pixels allocated on each tablet, based on the spectrums of the pixels, and to distinguish the type of tablet, based on the spectrums of the specified pixels. While some of the allocated pixels are allocated on the tablets, others are allocated between the tablets, with this method being for specifying pixels on the tablets by analyzing the spectrums of all the pixels. Since the spectrums of pixels allocated on the tablets are completely different from the spectrums of pixels allocated to the packaging material between the tablets, sorting can be easily performed.

Also, in the above drug inspection device, a pressing member that, with respect to a packaging material constituted by a sheet-like base material and the pockets which are formed in the base material, presses the base material can be further provided. Since such packaging material can suffer from warping, the packaging material could possibly lift up from the conveyance surface, making it difficult to focus during image capture by the imaging unit. In view of this, providing the above pressing member enables lifting up of the packaging material to be prevented and spectrum data to be accurately captured.

Also, a drug investigation method according to the present invention is for distinguishing types of tablets in a tablet packaging process for tablets containing different amounts of active pharmaceutical ingredients, every row or every pocket, in which a plurality of rows each having aligned therein a plurality of tablets housed in respective pockets are conveyed, and includes a step of irradiating the tablets with a light beam that includes near-infrared light, a step of dispersing the reflected light from the tablets to be incident on a spectroscope, a step of capturing, with a near-infrared imaging unit, a spectrum obtained through dispersion of the reflected light by the spectroscope, and generating image data, and a step of processing the image data and performing an operation for distinguishing the types of tablets. In the near-infrared imaging unit is configured to capture, with one image capture, the spectrums of a predetermined number of pixels allocated to a predetermined length in a direction in which the tablets are aligned in the row, and a control unit is configured to perform control such that the near-infrared imaging unit performs image capture at least once on the tablets included in the one row, to compute average spectrum data per tablet by averaging the spectrums of the pixels on a tablet surface every pocket, and to distinguish the type of tablet based on the average spectrum data.

Effect of Invention

As described above, the present invention enables types of tablets that have different amounts of active pharmaceutical ingredients and are indistinguishable in appearance, such as tablets manufactured for clinical trials, to be distinguished.

REFERENCE SIGN LIST

100 Packaging material
101 Tablet
102 Pocket portion
103 Base material
13 Light source (irradiation unit)
3 Spectroscope
4 Line sensor camera (near-infrared imaging unit)
5 Computer (control unit)

DESCRIPTION OF EMBODIMENTS

Figure 1:
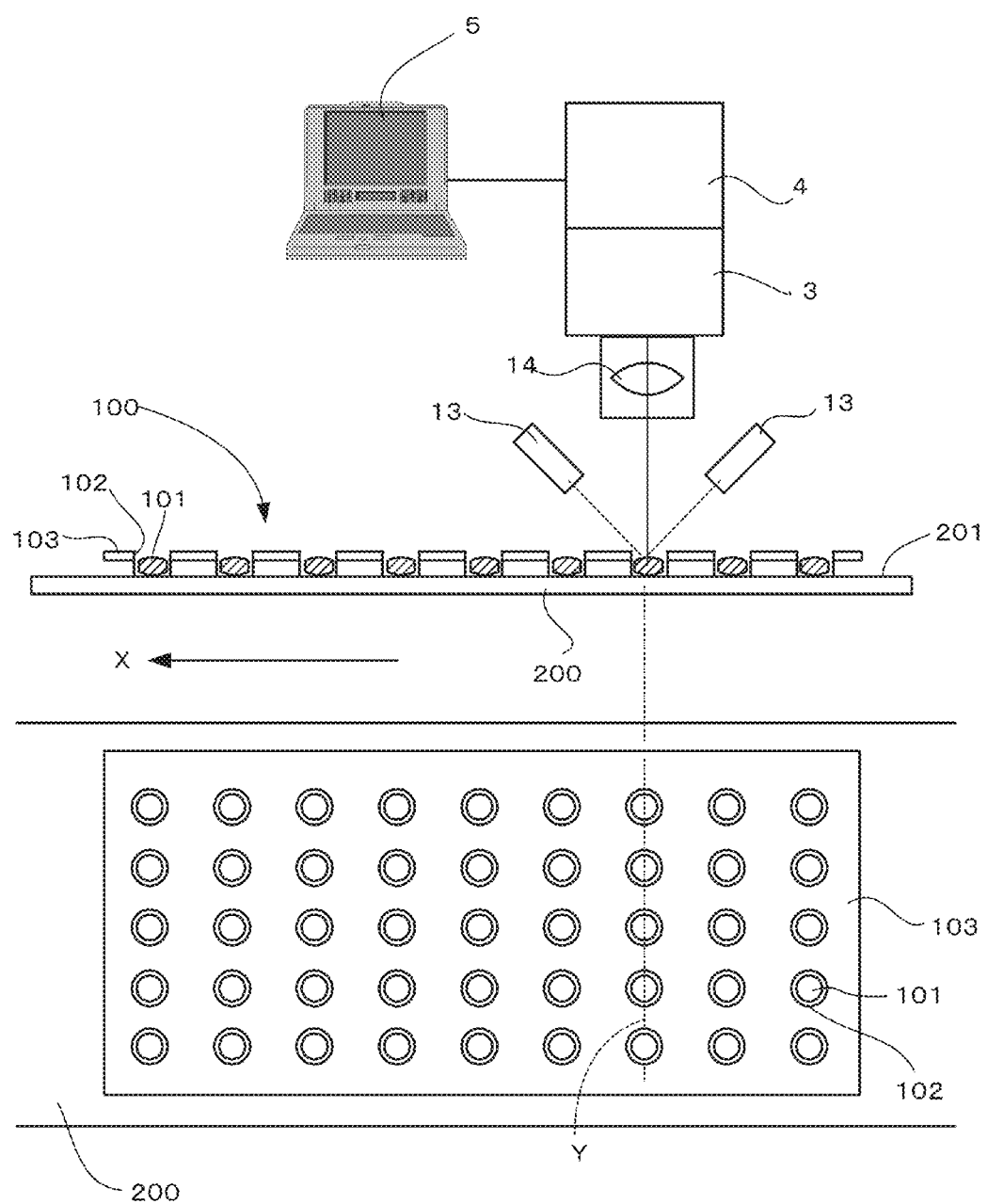
FIG. 1 is a schematic configuration diagram showing an embodiment of a drug inspection device according to the present invention (cross-sectional view and plan view of conveyance path).

Hereinafter, an embodiment of a drug inspection device according to the present invention will be described with reference to the drawings. FIG. 1 is a schematic configuration diagram of the drug inspection device according to the present embodiment.

The drug inspection device according to the present embodiment is for distinguishing types of tablets having different amounts of active pharmaceutical ingredients, mainly with respect to investigational drugs in tablet form. For example, with investigational drugs in tablet form, a plurality of types of tablets are housed in pocket portions of a packaging material (e.g., PTP sheets) provided in a plurality of rows. The tablets have amounts of active pharmaceutical ingredients that differ every row or every pocket, but are manufactured so as to be indistinguishable in appearance. The present embodiment is for inspecting such investigational drugs and checking that the correct drugs are housed in the correct positions. As shown in FIG. 1, a packaging material 100 targeted here has a plurality of rows that are arranged in a conveyance direction X, and a plurality of tablets 101 are housed in each row (five in the example shown in FIG. 1). In this packaging material 100, a plurality of transparent pocket portions 102 that each house a tablet 101 are formed in a sheet-like base material 103 made of PP, PVC or the like. While the upper surface of the sheet base material 103 is heat sealed with aluminum foil or the like and the pocket portions 102 are closed off after tablets have been housed, here, inspection which will discussed later is carried out when the tablets 101 are housed in the pocket portions 102 before being heat sealed with aluminum foil or the like. That is, the packaging material 100 thus formed is conveyed on a conveyance path 200 so that the pocket portions 102 project downward, and inspection is carried out with the tablets 101 open upward.

As shown in FIG. 1, this drug inspection device is provided with a lens 14, a spectroscope 3 and a line sensor camera 4 capable of capturing near-infrared light, all of which are installed above the conveyance path 200 of the packaging material 100. In addition, a computer 5 that performs driving of the device, data processing and the like is attached. Also, a pair of light sources 13 that irradiate the packaging material 100 with light beams (white light, etc.) that include near-infrared light are installed so as to sandwich the tablets of one row of the packaging material 100 in the conveyance direction. White halogen lamps that cover from a near-infrared to a far infrared region can be used as the light sources 13, for example.

Known devices can be used for the spectroscope 3 and the line sensor camera 4. For example, a line sensor camera having sufficient sensitivity to near-infrared light with a wavelength of roughly 900 to 2500 nm can be used for the line sensor camera 4. Also, the line sensor camera 4 is connected to the computer 5, and processing of the captured data is performed.

A storage unit (hard disk, SSD, etc.) of the computer 5 stores data relating to spectrums obtained from the tablets, as will be discussed later. That is, data showing the relationship between an average spectrum that is obtained and the type of drug based on the characteristics (e.g., shape and intensity of specific wavelength region) of the average spectrum is saved. Here, data is saved by drug type or data relating to drugs that are the same but have different amounts of ingredients is saved. Also, software that analyzes obtained average spectrum data is also saved. For example, in the case where obtained average spectrum data cannot be directly collated with saved data, the average spectrum data is processed by subjecting the average spectrum data to multivariate analysis (e.g., principal component analysis, etc.) so that the data can be readily collated with saved data.

Apart from being saved in a storage unit incorporated in the computer, the above data and software can also be saved in a storage medium such as a CD-ROM or a flash memory and read out from there. Furthermore, these data can also be saved in an external storage medium, and data can be read out for use on the computer 5 via a network. Accordingly, the storage unit of the present invention also includes a volatile memory that temporarily saves data read out from an external storage medium, in addition to a nonvolatile memory or a hard disk within the computer.

Figure 2:
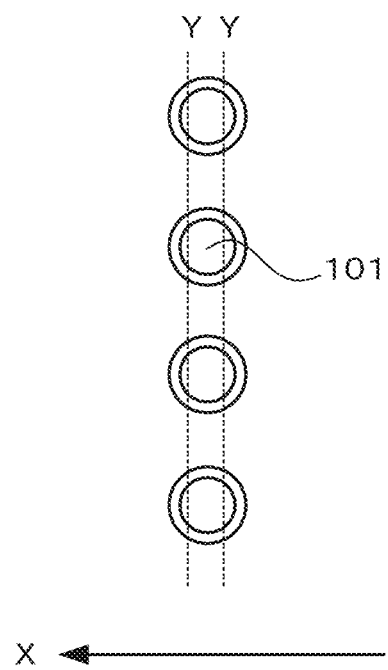
FIG. 2 is a plan view showing another example of image capture by a line sensor camera.

Next, a method for inspecting tablets using the above drug inspection device will be described. First, a packaging material 100 such as described above is disposed on the conveyance path 200, and conveyed in the conveyance direction X as shown in FIG. 1. Next, the light sources 13 irradiate one row of the tablets 101 with light beams that include near-infrared light. The light beams that include near-infrared light are reflected by the surface of the tablets 101, and the reflected light is sent to the spectroscope 3 after being focused by the lens 14. As described above, this device uses the line sensor camera 4, and image capture is performed with a predetermined number of pixels allocated to the row that is to be captured. For example, 320 pixels can be allocated per row. Although also dependant on the relationship between the conveyance speed of the conveyance path 200 and the shutter speed of the line sensor camera 4, a line Y to be captured with at least one image capture is positioned on the tablets 101 aligned in one row. At this time, image capture desirably is performed two or more times on the tablets 101 aligned in one row, as shown in FIG. 2.

Figure 3:
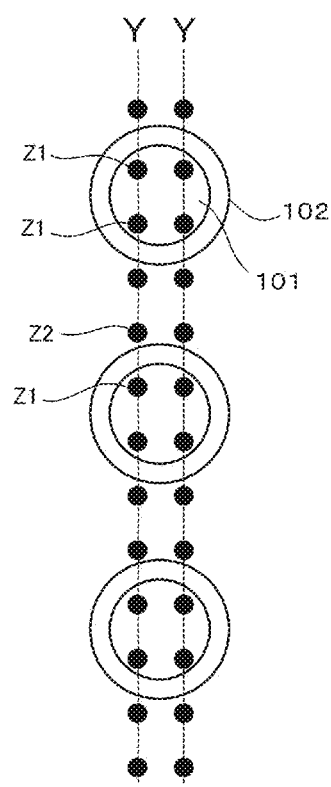
FIG. 3 illustrates allocation of pixels on tablets.

An optical spectrum is formed when the reflected light from a tablet is incident on the spectroscope 3. An image of this optical spectrum is formed on an imaging surface of the line sensor camera 4, and image data is sent to the computer 5. The following processing is performed by the computer 5. First, several to several tens of spectrums that are based on the pixels allocated to the surface of the tablet 101 are averaged and average spectrum data per tablet is computed. For example, in the case where four pixels $Z1$ are allocated per tablet 101, as shown in FIG. 3, the spectrums of these four pixels $Z1$ are averaged. Here, which pixel is on which tablet can be specified in advance from the conveyance speed of the tablets, the interval between pockets, the allocation interval of pixels, and the like. Accordingly, the spectrums that are obtained for each tablet 101 can be specified. Alternatively, the spectrums that are obtained for each tablet can also be specified after obtaining all the spectrums. This enables the spectrums of the pixels $Z1$ that are on the tablets 101 to be sorted out after measurement, since the spectrums of the pixels $Z1$ that are on the tablets 101 are completely different from the spectrums of pixels $Z2$ that are on the packaging material between the tablets 101.

Averaging is thus performed when the spectrums of the plurality of pixels on each tablet have been obtained, with an exemplary method of averaging being to compute the arithmetic mean. The arithmetic mean is computed by adding together the spectrums of the pixels obtained from the tablet surface, and dividing the resultant value by the number of pixels. When the average spectrum data per tablet has been obtained, this data is collated with the data saved in the storage unit, and the type of drug is thus distinguished. At this time, the type of drug can be distinguished by, for example, extracting the shape or intensity of a specific wavelength of the obtained average spectrum, and collating this data with the data in the storage unit. Types of tablets containing different amounts of active pharmaceutical ingredients every PTP pocket can thus be distinguished. However, there are cases where the type of drug cannot be distinguished from the average spectrum data obtained at this time. For example, one such case is where there is only a slight difference in the amounts of ingredients between drugs of the same type. In such cases, the obtained average spectrum data can be analyzed with the above software, and an attempt can be made to distinguish the type of drug using principal component analysis, for example. Types of tablets 101 containing different amounts of active pharmaceutical ingredients every PTP pocket can thus be distinguished.

According to the drug inspection device of the present embodiment, types of tablets having different amounts of active pharmaceutical ingredients can be distinguished using obtained spectrum data, even with tablets that are indistinguishable in appearance. As a result, whether the correct tablets have been prepared as an investigational drug can be fully inspected quickly and in a non-destructive manner. More specifically, although, with investigational drugs such as the above, different tablets may be housed in each row of the packaging material or different tablets may be housed within the one row, the types of tablets can be easily distinguished in either case.

In the above processing, since average spectrum data obtained by averaging the spectrums of the pixels of each tablet is used, the volume of data can be reduced and tablets can be distinguished quickly. Also, the device is suited to data transmission by wireless or the like, enabling device versatility to also be improved. Furthermore, reducing the volume of data enables power savings to be realized, even with regard to the load on the computer that saves the series of measurement results.

Although an embodiment of the present invention has been described above, the present invention is not limited to this embodiment, and various modifications are possible to the extent that they do not deviate from the gist of the invention. For example, although, in the above embodiment, spectrums are collected directly from the tablet surface by the lens 14 attached to the tip of the spectroscope 3, use of an embodiment shown in FIG. 4 enables the amounts of active pharmaceutical ingredients in tablets that have already been packaged in a PTP sheet to also be distinguished. With this device, the packaging material is disposed such that the pocket portions project upward, and reflected light that has passed through the plastic film of the pocket portions made of PP, PVC or the like is captured with the line sensor camera 4, instead of light reflected directly from the tablets. At this time, the distance between the line sensor camera 4 and the tablet 101 is adjusted so that the camera 4 is focused on the tablet. Reflected light from the tablet is sent to the line sensor camera 4 through the spectroscope 3, after being reflecting by the mirror 12. Note that a gold mirror having a high reflectivity of near-infrared light can be used as the mirror, for example. Data captured with the line sensor camera 4 is then processed by the computer 5, similarly to the above embodiment. Incidentally, since there is a high instance of warping with PTP sheet depending on the plastic material, the sheet itself could possibly lift up from the conveyance surface, making it difficult to focus during image capture by the line sensor camera 4, and preventing spectrum data from being accurately captured.

Figure 5:
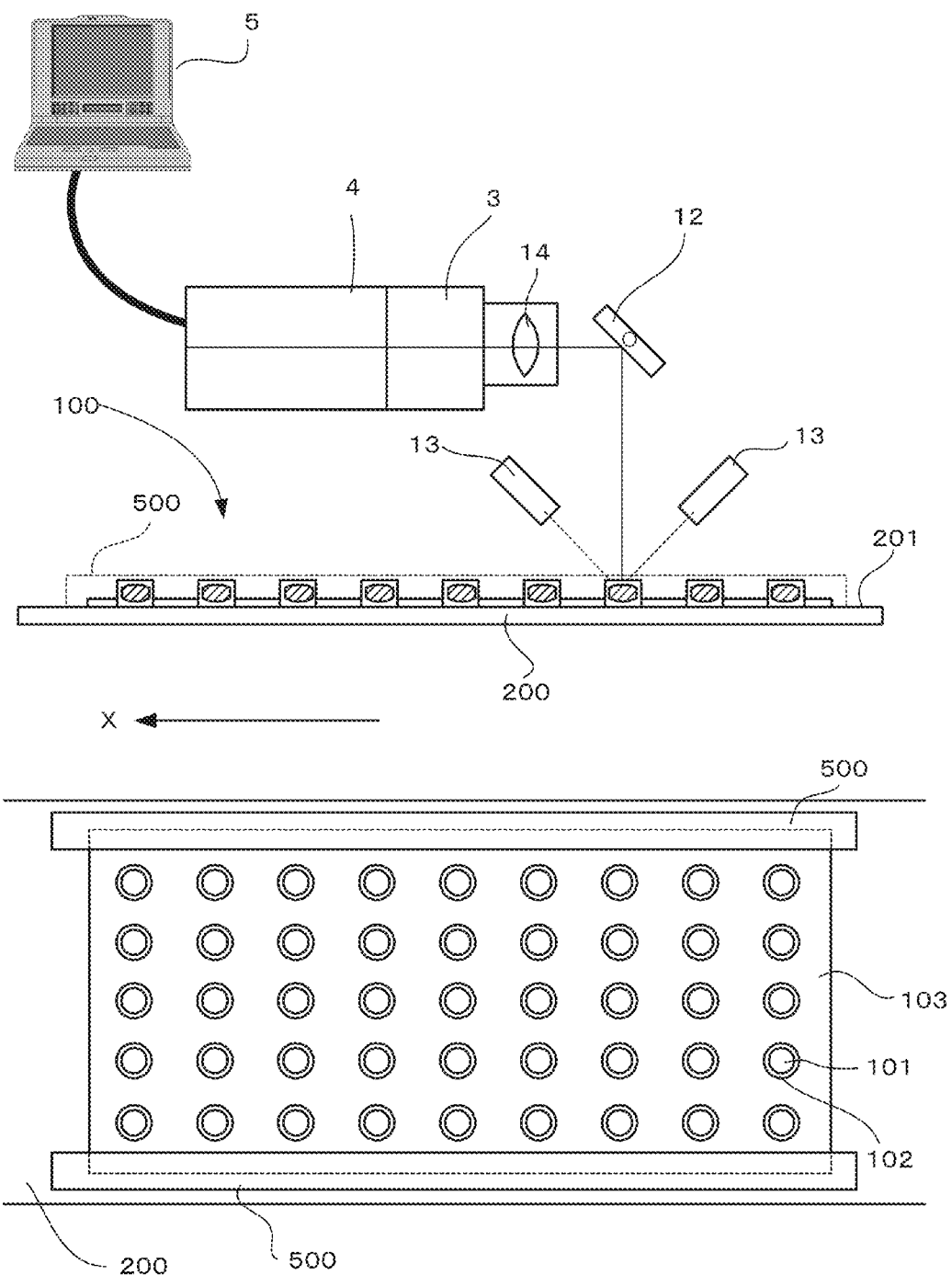
FIG. 5 is a cross-sectional view and a plan view showing an example of another drug inspection device.

In view of this, installing a pair of pressing members 500 on both edges of the conveyance path 200, as shown in FIG. 5, enables warping of the packaging material 100 to be reduced. These pressing members 500 reduce warping of the packaging material 100 by pressing down on the base material 103 of the packaging material 100 from above. The focal point of the line sensor camera 4 when capturing tablets can thereby always be kept constant. Thus, accurate image capture becomes possible, and the types of tablets can be distinguished more accurately. Note that the pressing members 500 may have any configuration that enables the base material 103 to be pressed down in a manner that does not obstruct conveyance of the packaging material 100. Also, although, in this example, the line sensor camera 4 is placed horizontally and captures reflected light from the mirror 12 that is incident horizontally, a mirror is not required in the case where the lens 14 of the line sensor camera 4 is placed vertically so as to face the tablets 101.

Figure 4:
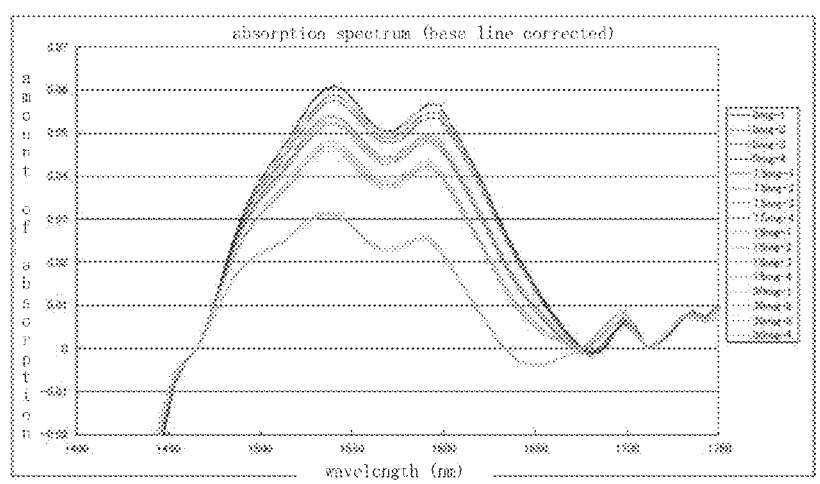
FIG. 4 is a graph showing the results of spectral analysis.
Figure 6:
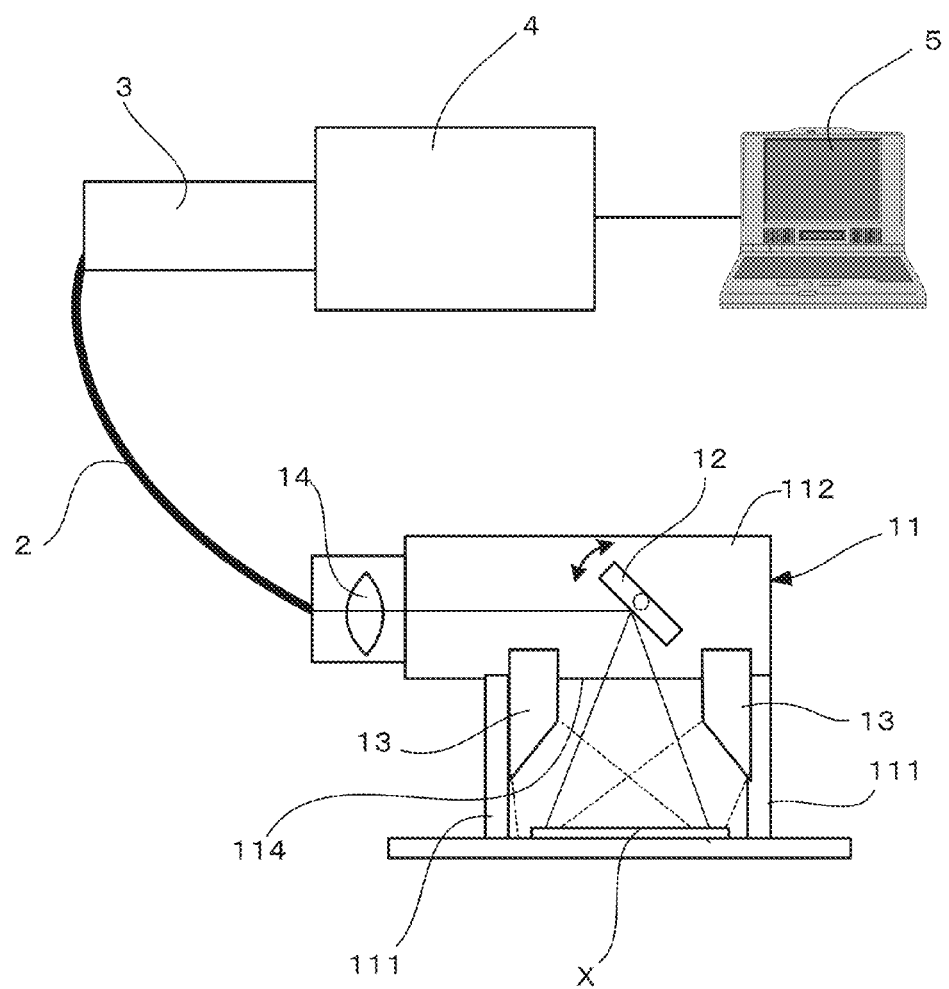
FIG. 6 is a cross-sectional view showing an example of another drug inspection device.

Also, the amounts of active pharmaceutical ingredients of tablets that have already been packaged in a PTP sheet can be distinguished, even using a device such as shown in FIG. 6. Although there is no conveyance system, the light sources 13 irradiates a PTP sheet X placed on a desk, for example, with light beams that include near-infrared light, and the mirror scanner 12 is driven and scans reflected light from the PTP sheet X. The reflected light thus obtained is sent to the line sensor camera 4 via the lens 14, the optical fiber 2 and the spectroscope 3, and image data is then sent to the computer 5. Next, in the computer 5, several to several tens of spectrums that are based on the pixels allocated to the tablet surface are averaged and average spectrum data per tablet is computed. Next, the type of drug is distinguished from the average spectrum data per tablet, with reference to a database. For example, spectrums such as shown in FIG. 4 can be detected, and the type of tablet for each PTP pocket can be distinguished by the shape or intensity of the spectrums. The amounts of active pharmaceutical ingredients can also be distinguished for each tablet by analyzing the data using a known method such as multivariate analysis (principal component analysis, etc.).

With the above device, since the type of each tablet can be distinguished, data that visualizes this can also be created. For example, images in which the types of tablets are distinguished by color can be displayed on the screen of the computer together the arrangement of tablets that is shown when displaying the analysis results, and this data can also be saved.

The invention claimed is:

1. A drug inspection device for distinguishing types of tablets in a tablet packaging process for tablets containing different amounts of active pharmaceutical ingredients, every row or every pocket, in which a plurality of rows each having aligned therein a plurality of tablets housed in respective pockets are conveyed, comprising:
    an irradiation unit configured to irradiate the tablets with a light beam that includes near-infrared light;
    a spectroscope on which reflected light from the tablets is incident;
    a near-infrared imaging unit configured to capture a spectrum obtained through dispersion of the reflected light by the spectroscope, and to generate image data; and
    a control unit configured to process the image data and to perform an operation for distinguishing the types of tablets,
    wherein the near-infrared imaging unit is configured to capture, with one image capture, the spectrums of a predetermined number of pixels allocated to a predetermined length in a direction in which the tablets are aligned in the row, and
    the control unit is configured to perform control such that the near-infrared imaging unit performs image capture at least once on the tablets included in the one row, to obtain a plurality of spectrums per one tablet by referring to each of pixels allocated on each tablet, to compute average spectrum data per tablet by averaging the plurality of spectrums of the pixels on a tablet surface every pocket, and to distinguish the type of tablets based on the average spectrum data.

2. The drug inspection device according to claim 1, wherein the control unit is configured to specify in advance one or more pixels allocated on each tablet, and to distinguish the type of the tablet based on the spectrums of the specified one or more pixels.

3. The drug inspection device according to claim 2, further comprising a pressing member configured to, with respect to a packaging material constituted by a sheet-like base material and the pockets which are formed in the base material, press the base material.

4. The drug inspection device according to claim 1, wherein the control unit is configured to specify pixels allocated on each tablet, based on the spectrums of the pixels, and to distinguish the type of the tablet based on the spectrums of the specified pixels.

5. The drug inspection device according to claim 4, further comprising a pressing member configured to, with respect to a packaging material constituted by a sheet-like base material and the pockets which are formed in the base material, press the base material.

6. The drug inspection device according to claim 1, further comprising a pressing member configured to, with respect to a packaging material constituted by a sheet-like base material and the pockets which are formed in the base material, press the base material.

7. A drug inspection method for distinguishing types of tablets in a tablet packaging process for tablets containing different amounts of active pharmaceutical ingredients, every row or every pocket, in which a plurality of rows each having aligned therein a plurality of tablets housed in respective pockets are conveyed, comprising the steps of:
    irradiating the tablets with a light beam that includes near-infrared light;
    dispersing the reflected light from the tablets to be incident on a spectroscope;
    capturing, with a near-infrared imaging unit, a spectrum obtained through dispersion of the reflected light by the spectroscope, and generating image data; and
    processing the image data and performing an operation for distinguishing the types of tablets, wherein the near-infrared imaging unit is configured to capture, with one image capture, the spectrums of a predetermined number of pixels allocated to a predetermined length in a direction in which the tablets are aligned in the row, and the control unit is configured to perform control such that the near-infrared imaging unit performs image capture at least once on the tablets included in the one row, to obtain a plurality of spectrums per one tablet by referring to each of pixels allocated on each tablet, to compute average spectrum data per the one tablet by averaging the plurality of spectrums of the pixels on a tablet surface every pocket, and to distinguish the type of tablet based on the average spectrum data.

* * * * *